United States Patent [19]

Beadle et al.

[11] Patent Number: 5,410,090
[45] Date of Patent: Apr. 25, 1995

[54] AIRLESS COBALT DEMETALLING IN THE COBALT FLASH COMBINATION CATALYST CYCLE

[75] Inventors: Stephen W. Beadle; William H. Summerlin, both of Baton Rouge, La.; Eddy T. A. Van Driessche, Eeklo, Belgium

[73] Assignee: Exxon Chemical Patents Inc., Linden, N.J.

[21] Appl. No.: 224,911

[22] Filed: Apr. 8, 1994

[51] Int. Cl.⁶ .................. C07C 45/50; C07C 45/78
[52] U.S. Cl. ........................ 568/451; 568/438; 568/452; 568/492
[58] Field of Search .......... 568/451, 452, 492, 438, 568/492

[56] References Cited

U.S. PATENT DOCUMENTS

| | | | |
|---|---|---|---|
| 2,744,921 | 5/1956 | Mertzweiler et al. | 260/414 |
| 2,816,933 | 12/1957 | Mertzweiller | 260/638 |
| 3,520,937 | 7/1970 | Moell et al. | 260/604 |
| 3,725,534 | 4/1973 | Reisch | 423/417 |
| 3,868,422 | 2/1975 | Hart et al. | 260/604 HF |
| 3,941,848 | 3/1976 | Kummer et al. | 260/604 HF |
| 4,390,473 | 6/1983 | Cooper | 260/429 R |
| 4,625,067 | 11/1986 | Hanin | 568/451 |
| 5,091,599 | 2/1992 | De Munck et al. | 568/882 |
| 5,235,112 | 8/1993 | Nodler et al. | 568/451 |
| 5,237,105 | 8/1993 | Summerlin | 568/451 |

FOREIGN PATENT DOCUMENTS

| | | |
|---|---|---|
| 0011842 | 1/1983 | European Pat. Off. |
| 0391650 | 10/1990 | European Pat. Off. |
| 1043097 | 9/1966 | United Kingdom |

*Primary Examiner*—Werren B. Lone
*Attorney, Agent, or Firm*—John J. Mahon

[57] ABSTRACT

A method for removing cobalt values from the crude product of a cobalt-catalyzed hydroformylation reaction by the application of an airless cobalt demetalling step upstream of the stripping step of a Cobalt Flash hydroformylation catalyst recovery process for $C_4$ to $C_{14}$ olefins, whereby no oxygen is required to oxidize cobalt carbonyls to their cobaltous form. This airless demetalling step may also be used downstream of the stripping step in the case of $C_7$ to $C_{20}$ olefins to remove carbonyls from a water soluble cobaltous salt and carbon carbonyl stream which is taken as bottoms from the stripper reactor.

21 Claims, 2 Drawing Sheets

AIRLESS COBALT DEMETALLING IN THE COBALT FLASH COMBINATION CATALYST CYCLE

A method for removing cobalt values from the crude product of a cobalt-catalyzed hydroformylation reaction by the application of an airless cobalt demetalling step either upstream or downstream of the stripping step of a Cobalt Flash hydroformylation catalyst recovery process. This unique demetalling step does not require the use of oxygen to oxidize cobalt carbonyls to their cobaltous form, rather it contacts the crude product with an aqueous stream containing an organic acid to convert the cobalt carbonyls to a water soluble cobaltous salt of the organic acid.

BACKGROUND OF THE INVENTION

Hydroformylation reactions involve the preparation of oxygenated organic compounds by the reaction of carbon monoxide and hydrogen (a.k.a., syn or synthesis gas) with carbon compounds containing olefinic unsaturation. The reaction is performed in the presence of a carbonylation catalyst and results in the formation of a compound, for example an aldehyde, which has one more carbon atom in its molecular structure than the starting olefinic feedstock. By way of example, higher alcohols may be produced in the so-called "oxo" process by hydroformylation of commercial $C_4$-$C_{14}$ olefin fractions to an aldehyde-containing oxonation product, which on hydrogenation yields respective $C_5$-$C_{15}$ saturated alcohols. The crude product of the hydroformylation reaction will contain catalyst, aldehydes, alcohols, unreacted feed, syn gas and by-products.

Before further processing of the crude product is possible, it is necessary to remove the catalyst therefrom. One conventional method of removing cobalt values from such a crude product is to treat the product with an alkali or acid wash technique. See Reisch U.S. Pat. No. 3,725,534, which issued on Apr. 3, 1973. However, this approach uses expensive raw materials and incurs problems associated with finally removing essentially all traces of cobalt from the water wash streams before being discharged. The Reisch process operates at a pressure of between 0-200 psig (0.1-1.48 MPa) and a temperature of between 82° C. to 121° C. for about 15-120 minutes.

Another conventional method involves the oxidation of the cobalt catalytic species followed by extraction as a cobalt salt in aqueous solution. See Mertzweiller et al. U.S. Pat. No. 2,744,921, which issued on May 8, 1956.

Hanin U.S. Pat. No. 4,625,067, which issued on Nov. 25, 1986, discloses still another method which involves the contacting of the crude product with a stream of stripping gas to entrain volatile cobalt compounds, characterized in that the contacting is performed in the presence of water and aqueous acid to dissolve those cobalt values not entrained in the gas under the conditions of temperature and pressure employed for the contacting, and the aqueous phase is subsequently separated from the organic hydroformylation reaction.

Although the stripping method disclosed in the Hanin patent overcomes the disposal and chemical additive costs of the caustic/acidification method of Reisch, it has the disadvantage that when lower carbon number olefins (e.g., $C_7$ and below) are used as the feedstock, unreacted compounds such as olefins and/or paraffins are stripped out together with the volatile cobalt compounds. These olefins and/or paraffins are then absorbed into the olefinic feedstock and recycled to the oxo reactor. This occurs because lower carbon number feedstocks such as heptene have roughly the same volatility as the cobalt specie, thereby causing it to be entrained together with the volatile cobalt and taken out overhead. Light hydrocarbons which are absorbed into the olefinic feedstock rapidly build up within the cobalt recovery system causing an undesirable decrease in net olefin feed rate.

Summerlin U.S. Pat. No. 5,237,105, which issued on Aug. 17, 1993, discloses a method of recovering cobalt values which does not cause the build up of unreacted light hydrocarbons within the system, thereby avoiding a decrease in the olefin feed rate. This is accomplished by providing a demetalling step prior to the stripping step which produces a substantially cobalt-free organic hydroformylation reaction product and water soluble cobaltous salt aqueous product. The organic hydroformylation reaction product is diverted for further downstream treatment, while the water soluble cobaltous salt aqueous product is concentrated, converted to cobalt carbonyl and stripped of volatile cobalts substantially free of any light hydrocarbons.

Summerlin U.S. Pat. No. 5,237,105, also discloses the removal of heptene and lighter grade cobalts from hydroformylation product by converting cobalt carbonyls to cobalt formate using air and a formic acid/water solution in a demetalling step disposed upstream of the stripper reactor. Summerlin also discloses the application of a demetalling step downstream of the stripper reactor which involves sending water stream bottoms from the stripper reactor, which typically contains trace levels of carbonyls, to the demetalling step to be mixed with crude oxo product and air at a temperature of 70°-100° C. and a pressure of 0.1-1.5 MPa for about 0.5-5 minutes. However, this results in the formation of an offgas which comprises oxygen-containing air which must be carefully controlled to prevent the formation of an explosive mixture. Moreover, the offgas must be safely disposed of, typically by means of a furnace.

The present invention removes the cobalt carbonyl catalyst using the demetalling step of the Summerlin patent, without the need for the addition of oxygen-containing air. That is, the present inventors have discovered that the demetalling of the hydroformylation product can be undertaken without oxygen-containing air, so long as the organic acid and water are mixed together with the hydroformylation reaction product at a moderate temperature and pressure for an appropriate length of time. This eliminates the need for the addition of air which can lead to yield losses and create problems concerning the safe disposal of the potentially oxygen-containing offgas. Moreover, the present invention avoids the need for a costly furnace to dispose of the offgas, since it no longer contains an explosive mixture of nitrogen and oxygen.

SUMMARY OF THE INVENTION

A Cobalt Flash demetalling combination catalyst cycle for removing cobalt from the crude hydroformylation product derived from heptene and lighter feedstocks, wherein the cobalt carbonyls are converted to water soluble cobalt formate by treating the hydroformylation product with a water stream containing an organic acid, e.g., formic or acetic acid without the addition of air, at a temperature of about 80° C. to 150° C. and a pressure of about 2 to 30 bar (0.2 to 3 MPa) for about 5 to 30 minutes. This airless demetalling process is also applicable to feedstocks heavier than heptene.

A method for removing cobalt values from the crude product of a cobalt-catalyzed hydroformylation reaction formed from an olefinic feedstock having a carbon number in the range between about $C_4$ to $C_{14}$ wherein an airless cobalt demetalling step which comprises the reacting of an oxo product, organic acid and $H_2O$ is disposed upstream of the stripping step of a Cobalt Flash hydroformylation catalyst recovery process. The crude oxo product typically containing cobalt compounds in addition to an organic hydroformylation reaction product.

Another method for removing cobalt values from the crude product of a cobalt-catalyzed hydroformylation reaction formed from an olefinic feedstock having a carbon number in the range between about $C_7$ to $C_{20}$, more preferably in the range between about $C_7$ to $C_{14}$, wherein an airless cobalt demetalling step which comprises the reacting of an organic acid, $H_2O$, a water soluble cobaltous salt containing trace amounts of a water soluble cobalt carbonyl, and, optionally, a cobalt-free organic hydroformylation product, is disposed downstream of the stripping step of a Cobalt Flash hydroformylation catalyst recovery process.

DESCRIPTION OF THE PREFERRED EMBODIMENTS

Figure 1:
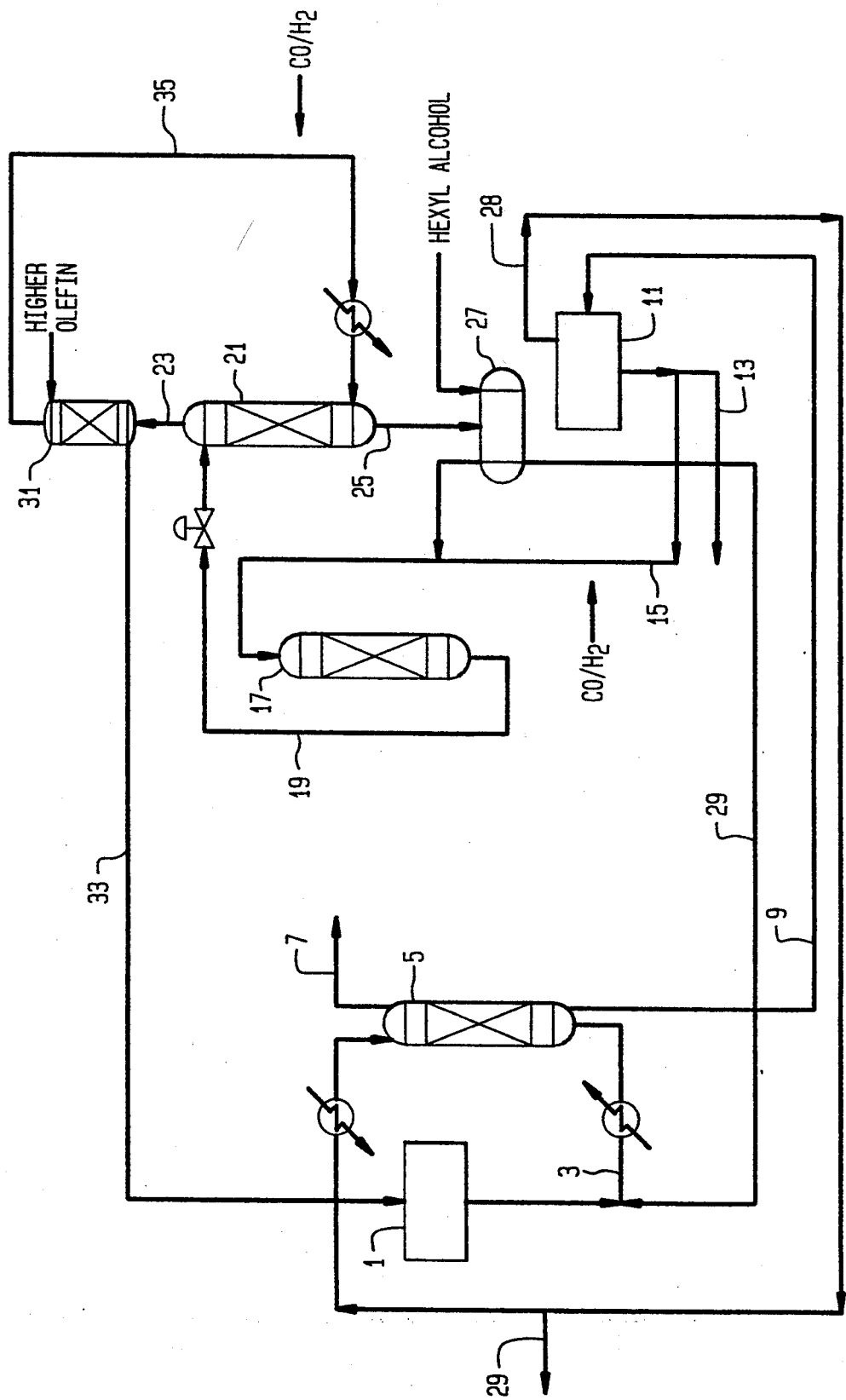
FIG. 1 is a flow diagram of a hydroformylation reaction system embodying the process of the present invention which is capable of removing cobalt values from crude products formed from an olefinic feedstock having a carbon number in the range from about $C_4$ to $C_{14}$, wherein an airless cobalt demetalling step which comprises the reacting of an oxo product, organic acid and $H_2O$ is disposed upstream of the stripping step of a Cobalt Flash hydroformylation catalyst recovery process.

Cobalt values can now be successfully removed from crude product of a cobalt-catalyzed hydroformylation reaction from olefinic feedstock without olefinic or paraffin build up during Cobalt Flash catalyst recovery cycles, especially when light hydrocarbons are used as the feedstock. This is accomplished by adding an airless cobalt demetalling step to the Cobalt Flash catalyst recovery cycle. One particularly suitable Cobalt Flash catalyst recovery cycle is set forth in Hanin U.S. Pat. No. 4,625,067, which is incorporated herein by reference.

The airless cobalt demetalling step according to one embodiment of the present invention is capable of converting cobalt carbonyl to a water soluble cobaltous salt that may be readily separated from organic hydroformylation reaction product such that only the dissolved cobaltous salts after it has been mixed with a recycling alcohol, e.g., hexyl alcohol, and converted to a cobalt carbonyl is passed on to the stripper reactor, thereby avoiding the entrainment of lighter hydrocarbons with the volatile cobalts.

In accordance with the preferred embodiment of the present invention (i.e., the application of an airless cobalt demetalling step upstream of the stripping step of a Cobalt Flash hydroformylation catalyst recovery process) water and an organic acid (e.g., formic acid) are mixed with the crude oxo product from an oxo reactor within a packed or trayed tower or in a pipe-reactor, at a temperature of about 80° C. to 150° C. and a pressure of about 2 to 30 bar (0.2 to 3 MPa) for about 5 to 30 minutes, in order to provide sufficient mixing and residence time without the use of air. The water stream containing a water soluble cobaltous salt is thereafter separated from the now cobalt-free organic hydroformylation reaction product which is sent directly to hydrogenation thus bypassing the conventional stripping step. The water soluble cobaltous salt is thereafter mixed with the water stream bottoms from the stripper reactor which also contains a cobaltous salt product and these combined streams are fed to an evaporator. More preferably, the water stream bottoms from the stripper reactor can be mixed with the crude oxo product upstream of the demetalling step. The evaporator concentrates the cobaltous salt and generates an overhead stream of cobalt-free water and organic acid which are recycled as wash water and for use in the demetalling step. The concentrated cobaltous salt stream is mixed with an alcohol stream and fed to a preforming reactor where the cobaltous salt is converted to cobalt carbonyls and then fed to the stripper reactor where the cobalt is stripped overhead using synthesis gas and then absorbed in the feed olefin. The alcohol stream is preferably taken from the bottoms stream of the stripper reactor and recycled back to the preformer reactor.

Accordingly, substantially all of the organic hydroformylation product is separated from the cobaltous salt aqueous product wherein the organic hydroformylation product bypasses the stripper reactor and is sent directly to a hydrogenation or distillation step. As such, the lighter hydrocarbons do not enter the stripper reactor and therefore cannot be entrained together with volatile cobalt. Since the lighter hydrocarbons are not entrained within the volatile cobalt they cannot be absorbed into the olefin feedstock and thus neither build up within the catalyst recovery cycle nor do they effect the net olefin feed rate.

Accordingly, cobalt values are removed from the crude hydroformylation product of a cobalt catalyzed hydroformylation reaction by contacting the crude oxo product with a stream of stripping gas to entrain volatile cobalt compounds, characterized in that the contacting is performed in the presence of water and organic acid to dissolve those cobalt values not entrained in the gas under the conditions of temperature and pressure employed for the contacting, and the aqueous phase is subsequently separated from the organic hydroformylation reaction product.

An alternative embodiment of this invention includes the application of an airless cobalt demetalling step downstream of the stripping step of a Cobalt Flash hydroformylation catalyst recovery process. This embodiment is particularly useful in decobalting heavier hydrocarbons (i.e., heavier than heptene). In accordance with this embodiment, crude hydroformylation product bypasses the demetalling step and, after addition of an organic acid and water goes directly to the stripper reactor where approximately 70% of the cobalt is stripped overhead as cobalt carbonyl using synthesis gas. The cobalt taken overhead is subsequently absorbed into the feed olefin.

The remaining cobalt leaves the stripper reactor as a mixture of an aqueous phase cobaltous salt and an organic phase cobalt-free hydroformylation reaction product via the bottoms stream. The aqueous phase cobaltous salt along with recycled wash water is then routed to the demetalling step to remove any trace levels of cobalt carbonyls. It may also be necessary to add additional organic acid and at least a portion of the cobalt-free organic hydroformylation reaction product to the aqueous phase cobaltous salt in order to allow the demetalling reaction to proceed.

The demetalled water stream is then diverted to the evaporator and concentrated. This concentrated cobaltous salt is thereafter mixed with a portion of the cobalt-free organic hydroformylation reaction product from the stripper bottoms stream, or an alcohol product, or recycled hydrogenation product and fed to the preforming reactor. Alternatively, a portion of the concentrated cobaltous salt is returned to the oxo reactor. The preformer product is mixed with the crude hydroformylation product from the oxo reactor and, optionally, the cobalt-free hydroformylation reaction product taken overhead from the demetalling step, and thereafter fed to the stripper reactor.

Contrary to upstream use of the demetalling step, downstream use permits the organic hydroformylation product to enter the stripper reactor wherein volatile cobalt is entrained in the stripping gas and the organics are taken out as bottoms. As discussed above, downstream use of an airless demetalling step is acceptable for treating hydroformylation product prepared from olefins having a carbon number of seven or greater. Lighter hydrocarbons would get entrained within the stripping gas and build up within the olefin feed of the catalyst recovery cycle. However, the present inventor has discovered that routing of the water soluble cobaltous salt taken as bottoms from the stripper reactor, together with a portion of the cobalt-free organic hydroformylation reaction product from the stripper bottoms stream, to a downstream airless demetalling step removes any trace levels of cobalt carbonyls and thus improves the overall performance of the recovery cycle.

In accordance with either mode of operation, the demetalling step is preferably followed by a preformer reactor. The concentrated cobaltous salt is catalytically reacted within the preformer reactor to product cobalt carbonyl. This cobalt carbonyl is then sent along with the crude oxo product to the stripper reactor. Here the stripping gas carries off the volatile cobalt carbonyls (including those newly introduced to the system from the cobalt preformer) and, which are then absorbed into the olefin feed before being returned to the oxo reactor. As a result only minimal quantities of fresh cobalt need be introduced into the oxo reactor as make up for an otherwise closed system.

The demetalling reactor preferably includes inert solid surfaces or trays to facilitate contact between the liquid and gas phases. That is, the demetalling reactor is preferably a packed or trayed column, pipe-reactor or any other vessel which provides sufficient mixing and residence time without the use of air. During the demetalling step, the hydroformylation product following cooling/heating to about 80° C. and pressurizing to about 10 barg (1.1013 MPa) is contacted with an aqueous stream containing an organic acid such as formic or acetic acid. The reactants are preferably heated and maintained at a temperature in the range between about 80°–150° C. and the pressure can be increased to approximately 30 bar (3 MPa) in order for the reaction to proceed. Proper mixing of the phases together with proper heating are necessary for the reactions by which the cobalt carbonyls are converted to the cobaltous salt of the organic acid to proceed and for transfer of the cobaltous salts into the aqueous phase. The mixing preferably occurs in a countercurrent manner within a packed column to provide sufficient contact time, i.e., 10–30 minutes, between the reactants, thereby insuring the necessary conversion of cobalt carbonyl to its cobaltous salt form. The amount of water required is approximately 5–50 wt. %, based upon the organic feed rate, whereas the amount of organic acid required is approximately 0.1–5 wt. %, based upon the organic feed rate.

When a packed column is used as the demetalling reactor, the hydroformylation product at the proper temperature is introduced at the bottom of the column and will contact the downward flowing aqueous phase which was introduced at the top of the column with the two phases having been continuously mixed by the packing material or trays. The organic product now essentially cobalt-free will be either sent to hydrogenation directly or further water washed to remove any traces of cobalt. The aqueous phase now containing cobalt formate (if formic acid is used) can now be concentrated and recycled back into the process. Any carbon monoxide or hydrogen produced can be vented from the top of the column. A stream of syn gas or any inert gas can be sparged into the column if required to enhance the conversion of the carbonyl to the salt. No oxygen is required to oxidize the cobalt carbonyls ($Co^{-1}$ or $CO^{-0}$) to the cobaltous ($Co^{+2}$) form.

The invention may be better understood by reference to the drawings, wherein FIG. 1 illustrates a method for removing cobalt values wherein an airless cobalt demetalling step is disposed upstream of the stripping step in a Cobalt Flash process.

FIG. 1 generally depicts a method for removing cobalt values from the crude product of a cobalt-catalyzed hydroformylation reaction formed from an olefinic feedstock having a carbon number in the range $C_4$–$C_{14}$, preferably $C_5$–$C_7$. The crude product typically contains cobalt compounds in addition to an organic hydroformylation reaction product.

An olefin feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 3 to packed or trayed column 5 (column 5 may alternatively be a mixing tube such as a pipe reactor) where it is contacted with a stream of organic acid (e.g., formic or acetic acid) and water, thereby producing a substantially cobalt-free organic hydroformylation reaction product and a water soluble cobaltous salt aqueous product. The water soluble cobaltous salt aqueous product is the reaction product of the cobalt carbonyls contained within the crude hydroformylation product and the water stream containing the organic acid. If a column 5 is used as the reactor, the crude hydroformylation product at the proper temperature is introduced near the bottom of column 5 and will contact the downward flowing aqueous phase (i.e., water and organic acid) which is introduced near the top of column 5 via conduit 4 such that the two phases are continuously mixed by means of the packing material or trays (not shown) or by counter-current mixing in a pipe reactor. Any carbon monoxide or hydrogen produced can be vented from the top of column 5 and either recycled or sent to a fuels disposition. If additional mixing is required to enhance the reaction a stream of syn gas or any inert gas can be sparged into column 5. The substantially cobalt-free crude product is now essentially cobalt-free and is taken overhead via conduit 7 for further downstream treatment such as distillation or hydrogenation. The water soluble cobaltous salt aqueous product is carried via conduit 9 to evaporator 11 which concentrates the water soluble cobaltous salt, thereby producing a concentrated aqueous solution of cobaltous salt and a substantially cobalt-free water containing the organic acid, whereby the concentrated aqueous solution of cobaltous salt is separated from the substantially cobalt-free water containing the organic acid. The substantially cobalt-free water containing the organic acid is taken overhead from evaporator 11 via conduit 28 and is used for washing via conduit 29 and/or mixed with additional organic acid and added to packed or trayed column 5 via conduit 4. Evaporator bottoms containing cobalt are recycled via conduit 13 to oxo reactor 1 and sent to preformer 17 via conduit 15. Whereas the concentrated aqueous solution of cobaltous salt is contacted with an alcohol stream and synthesis gas within conduit 15 before this mixture is passed to preformer reactor 17. In preformer reactor 17 the concentrated aqueous solution of cobaltous salt is converted to a cobalt carbonyl under catalytic conditions. The cobalt carbonyl from preformer reactor 17 is carried via conduit 19 to stripper reactor 21 where it is contacted with a stream of stripping gas at a temperature of not greater than 100° C. and at a pressure below 10.13 bar (1.013 MPa), the pressure being lower than the decomposition pressure of the cobalt compounds at the contacting temperature, to entrain volatile cobalt compounds in the stripping gas and to generate as bottoms alcohol products and dissolved cobaltous salts; whereby the entrained volatile cobalt compounds are taken out overhead via conduit 23 and the alcohol products and dissolved cobaltous salts are taken out as bottoms via conduit 25. The alcohol products are separated from the dissolved cobaltous salts in settling drum 27. The dissolved cobaltous salts are typically in an aqueous phase, e.g., an aqueous salt product, which can be readily separated from the organic phase, i.e., the alcohol products, by gravity settling. The alcohol products from settling drum 27 are preferably recycled to conduit 15 for mixing with the cobaltous salt upstream of preformer reactor 17. The cobaltous salt from settling drum 27 is preferably recycled via conduit 29 to conduit 3 for further demetalling. Finally, the volatile cobalt compounds from conduit 23 are introduced into absorber 31 where they are contacted with olefinic feedstock, whereby the volatile cobalt compounds are absorbed into the olefinic feedstock and recycled to oxo reactor 1 via conduit 33. Cobalt-free gas from absorber 31 is returned to stripper reactor 21 via conduit 35. Optionally, syn gas may also be fed into stripper reactor 21 via conduit 35.

The organic acid introduced into column 5 via conduit 4 for use in the airless cobalt demetalling step is typically selected from the group consisting of: formic acid, acetic acid, propionic acid, and other acids having a boiling point approximately the same as water such that appreciable values of acid can be recovered in evaporator 27 for recycling to conduit 3 via conduit 29. It is most preferable that the organic acid be formic acid such that the resultant water soluble cobaltous salt is cobalt formate. The amount of organic acid which is added to the crude oxo product is a function of the amount of cobalt contained within the crude oxo product. Cobalt Flash processes are designed to use 140% of theoretical organic acid to convert cobalt carbonyl to cobalt formate. For example, formic acid may be added to the crude oxo product in an amount of about 2.18 grams of formic acid/gram of cobalt. Thus, if the cobalt concentration in the crude oxo product is in the range between about 0.05 to 0.50 weight %, then the formic acid is preferably added to the crude oxo product in an amount between about 1.09 to 10.9 milligrams of formic acid/gram of crude oxo product.

It is preferred that the concentration of the water soluble cobaltous salt aqueous product take place in either a flash unit or evaporator 11 by means of distillation or membrane separation.

Although it is preferable to convert the concentrated aqueous solution of cobaltous salt to a cobalt carbonyl in the presence of a noble metal catalyst disposed within preformer reactor 17, it is optional to convert by contacting of phases at a pressure in the range between about 10.3 MPa (i.e., 1500 psig) to 31 MPa (i.e., 4500 psig) and a temperature in the range between about 100° C. to 150° C.

It is also optional to subject the substantially cobalt-free organic hydroformylation reaction product diverted from column 5 to a water wash treatment in order to remove residual cobalt values remaining therein prior to further downstream treatment such as distillation or hydrogenation. The water introduced in the airless cobalt demetalling step via conduit 4 is used in a water to crude product weight ratio of from 0.05:1 to 0.5:1. This ratio is based upon the assumption that 1 wt. % cobalt concentration (as cobalt, not cobalt formate) in water is desirable.

Figure 2:
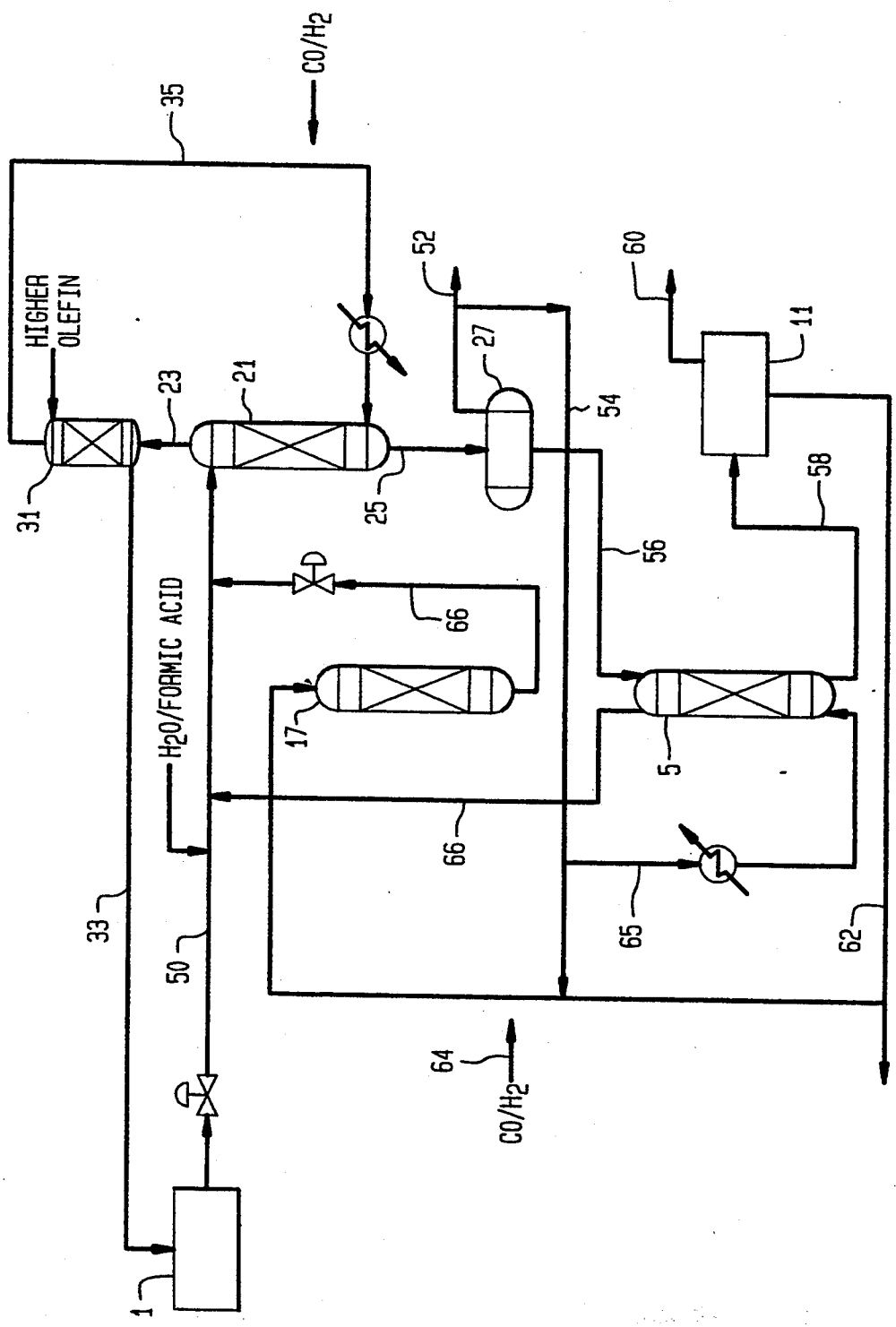
FIG. 2 is a flow diagram of a hydroformylation reaction system embodying another embodiment of the process of the present invention which is capable of removing cobalt values from crude products formed from an olefinic feedstock having a carbon number in the range from about $C_7$ to $C_{14}$, wherein an airless cobalt demetalling step which converts trace levels of cobalt carbonyl found in the water phase of the stripper reactor bottoms to a water soluble cobaltous salt is disposed downstream of the stripping step of a Cobalt Flash hydroformylation catalyst recovery process.

FIG. 2 depicts a method for removing cobalt values from the crude product of a cobalt-catalyzed hydroformylation reaction formed from an olefinic feedstock having a carbon number in the range of $C_7$-$C_{14}$, wherein an airless cobalt demetalling step is disposed downstream of the stripping step in a Cobalt Flash process.

An olefin feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 50 where it is contacted with water and an organic acid which is delivered via conduit 60 from evaporator 11. This water and organic acid, which is delivered via conduit 60, is used to wash gas streams not shown, thereby providing the water and organic acid which are necessary for the stripper reactor 21 to perform satisfactorily. The treated crude product is thereafter contacted with a stream of stripping gas in stripper reactor 21. The stripping typically occurs at a temperature of not greater than 100° C. and at a pressure below 10.13 bar (1.013 MPa), the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products containing water soluble cobaltous salts and trace amount of water soluble cobalt carbonyl dissolved therein are taken out as bottoms via conduit 25. The water soluble cobaltous salt and cobalt carbonyl are then separated from the organic hydroformylation reaction products by means of settling drum 27. The cobalt-free organic hydroformylation reaction product is then carried via conduit 52 for further downstream treatment such as distillation or hydrogenation. Optionally, a portion of the organic hydroformylation product may be diverted from conduit 52 via conduit 54 and recycled to the preformer reactor 17. The water soluble cobaltous salt and trace levels of carbon carbonyl are carried via conduit 56 to demetalling column 5 where they are optionally contacted with additional organic acid makeup. The water soluble cobaltous salt and cobalt carbonyl are also preferably contacted, in a countercurrent manner, with a portion of cobalt-free hydroformylation reaction product supplied via conduits 52, 54 and 65. The presence of an organic phase, such as the cobalt-free hydroformylation reaction product, is necessary in order for the airless demetalling reaction to proceed. That is, in conventional downstream demetalling systems it would not be feasible to remove the air stream since there is no organic phase present in those demetalling steps. The present inventors have determined that an organic phase is necessary in order to insure that the disproportionation reaction proceeds during demetalling, otherwise cobalt carbonyl crystals [$Co_2(CO)_8$] will form, cobalt will plate, and/or $HCo(CO)_4$ will appear in the evaporator overhead. The diversion of a small slipstream of recycled cobalt-free hydroformylation product from conduits 52, 54 and 65 (in an amount of 10-50% volume on water) to demetalling column 5 will overcome the problems of the conventional systems. Once the cobalt-free hydroformylation reaction product exits column 5 it can be routed back to stripper-reactor 21 via conduit 66.

Thereafter, the water soluble cobaltous salt aqueous product is carried via conduit 58 to evaporator 11 which forms a concentrated aqueous solution of cobaltous salt and a substantially cobalt-free water containing the organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed on to preformer reactor 17 where the concentrated aqueous solution of cobaltous salt is converted to a cobalt carbonyl. The cobalt carbonyl is then carried via conduits 66 and 50 to stripper reactor 21. Finally, the volatile cobalt compounds which are carried from stripper reactor 21 via conduit 23 are sent to absorber 31 wherein they are absorbed into the olefinic feedstock and returned to oxo reactor 1 via conduit 33.

It is preferable that the operating conditions in airless demetalling column 5 (i.e., a pipe reactor) be as follows:
Inlet Pressure: 20-450 psig (0.239-3.204 MPa)
Temperature: 66°-150° C.
Residence Time: 0.5-60 minutes
Contacting Means: Counter-Current Flow
Percent $H_2O$: Approximately 20 vol. %

For complete carbonyl removal a temperature of 150° C. is required, together with the addition of 2% free formic acid to the inlet water stream.

EXAMPLE 1

Nonene feed containing 0.29 wt. % cobalt was hydroformylated at 175° C. and a pressure of 300 barg (30.1013 MPa). After pressure reduction and cooling to 30 barg (3.1013 MPa) and 150° C., respectively, water was added at 20 volume % with the water stream which contains 1.93 wt. % free formic acid and this mixture is then introduced into a fully turbulent pipe reactor having a residence time of approximately 2 minutes. Good mixing was achieved via pressure drop in the pipe reactor (exiting pressure was 6 barg (0.7013 MPa)). Analysis of the exiting organic/water phases revealed:
Organic Phase (total Co, wt. %) 0.0016
Water Phase ($Co^{-1}$(carbonyl), wt. %) <0.0001
Water Phase, ($Co^{+2}$, wt. %) 0.908

Of the entering cobalt, 99.4 wt. % was transferred to the water phase and essentially all of the cobalt carbonyls converted to $Co^{+2}$. The exiting water phase also contained 0.76 wt. % free formic acid the balance reacting with the cobalt to form cobalt formate. The trace levels of cobalt in the organic phase were subsequently reduced further by a single water wash step resulting in an essentially cobalt-free organic product.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for removing cobalt values from the crude product of a cobalt-catalyzed hydroformylation reaction formed from an olefinic feedstock, said crude product containing cobalt compounds in addition to an organic hydroformylation reaction product, which comprises:
   a. contacting said crude product with an organic acid and water, in the absence of any oxygen-containing gases, thereby producing a substantially cobalt-free organic hydroformylation reaction product and a water soluble cobaltous salt aqueous product;
   b. separating said substantially cobalt-free crude product from said water soluble cobaltous salt aqueous product;
   c. diverting said substantially cobalt-free organic hydroformylation reaction product for further downstream treatment such as distillation or hydrogenation;
   d. concentrating said water soluble cobaltous salt aqueous product thereby producing a concentrated aqueous solution of cobaltous salt and a substantially cobalt-free water containing said organic acid, whereby said concentrated aqueous solution of cobaltous salt is separated from said substantially cobalt-free water containing said organic acid;

e. recycling said substantially cobalt-free water containing said organic acid to step (a);

f. contacting said concentrated aqueous solution of cobaltous salt with an alcohol stream and synthesis gas, and passing this mixture to a preformer reactor where said concentrated aqueous solution of cobaltous salt is converted to a cobalt carbonyl;

g. contacting said cobalt carbonyl with a stream of stripping gas to entrain volatile cobalt compounds in said stripping gas and to generate as bottoms alcohol products and dissolved cobaltous salts, whereby said entrained volatile cobalt compounds are taken out overhead and the alcohol products and dissolved cobaltous salts are taken out as bottoms;

h. separating said alcohol products of step (g) from said dissolved cobaltous salts;

i. recycling said alcohol products from step (h) to step (f);

j. recycling said dissolved cobaltous salts from step (h) to step (a); and k. contacting said volatile cobalt compounds from step (g) with said olefinic feedstock, whereby said volatile cobalt compounds are absorbed into said olefinic feedstock.

2. The method according to claim 1 wherein said crude product is heated/cooled to between about 80° to 150° C. and pressurized to between about 0.3013 to 3.1013 MPa prior to step (a).

3. The method according to claim 1 wherein said contacting step (a) occurs at a temperature in the range between about 80° to 150° C.

4. The method according to claim 1 wherein contacting step (a) and separating step (b) occur in a packed or trayed column.

5. The method according to claim 1 wherein contacting step (a) and separating step (b) occur in a pipe-reactor.

6. The method according to claim 1 wherein said crude product is contacted in step (a) with said organic acid and said water for about 5 to 30 minutes.

7. The method according to claim 1 wherein contacting step (a) includes water in an amount between about 5 to 50 wt. %, based upon the feed rate of said crude product, and said organic acid in an amount between about 0.1 to 5 wt. %, based upon the feed rate of said crude product.

8. A method for removing cobalt values from the crude product of a cobalt-catalyzed hydroformylation reaction formed from an olefinic feedstock, said crude product containing cobalt compounds in addition to an organic hydroformylation reaction products which comprises:

a. contacting said crude product with water and an organic acid;

b. contacting the product of step (a) with a stream of stripping gas to entrain volatile cobalt compounds in said stripping gas; whereby said entrained volatile cobalt compounds are taken out overhead, and organic hydroformylation reaction products containing water soluble cobaltous salts and water soluble cobalt carbonyl dissolved therein are taken out as bottoms;

c. separating said water soluble cobaltous salts and said water soluble cobalt carbonyl of step (b) from said organic hydroformylation reaction products;

d. diverting at least a portion of said organic hydroformylation reaction product of step (c) for further downstream treatment such as distillation or hydrogenation;

e. contacting said water soluble cobaltous salts and said water soluble cobalt carbonyl of step (c) with an organic acid, water and at least a portion of said organic hydroformylation reaction product of step (c), in the absence of any oxygen-containing gases, thereby converting said water soluble cobalt carbonyl to a cobaltous salt and forming a water soluble cobaltous salt aqueous product;

f. concentrating the water soluble cobaltous salt aqueous product from step (e) thereby producing a concentrated aqueous solution of cobaltous salt and a substantially cobalt-free water containing said organic acid, whereby said concentrated aqueous solution of cobaltous salt is separated from said substantially cobalt-free water containing said organic acid;

g. recycling said substantially cobalt-free water containing said organic acid to step (b);

h. contacting at least a portion of said concentrated aqueous solution of cobaltous salt with an alcohol stream, an oxonation product and/or a hydrogenation product and synthesis gas, and passing this mixture to a preformer reactor where said concentrated aqueous solution of cobaltous salt is converted to a cobalt carbonyl;

i. recycling the cobalt carbonyl produced in step (h) to step (a); and j. contacting said volatile cobalt compounds from step (b) with said olefinic feedstock, whereby said volatile cobalt compounds are absorbed into said olefinic feedstock.

9. The method according to claim 8 wherein said crude product is either cooled/heated to between about 80° to 150° C. and pressurized to between about 0.3013 to 3.1013 MPa prior to step (e).

10. The method according to claim 8 wherein said contacting step (e) occurs at a temperature in the range between about 80° to 150° C.

11. The method according to claim 8 wherein contacting step (e) occurs in a packed or trayed column.

12. The method according to claim 8 wherein contacting step (e) occurs in a pipe-reactor.

13. The method according to claim 8 wherein said crude product is contacted in step (e) with said organic acid, water and organic hydroformylation reaction product for about 5 to 30 minutes.

14. The method according to claim 8 wherein contacting step (e) includes water in an amount between about 5 to 50 wt. %, based upon the feed rate of said crude product, and said organic acid in an amount between about 0.1 to 5 wt. %, based upon the feed rate of said crude product.

15. The method according to claim 8 wherein step (e) also produces a substantially cobalt-free hydroformylation product which is recycled to step (b).

16. A method for removing cobalt values from the crude product of a cobalt-catalyzed hydroformylation reaction formed from an olefinic feedstock, said crude product containing cobalt compounds in addition to an organic hydroformylation reaction product, which comprises demetalling said crude product by contacting said crude product with an organic acid and water, in the absence of any oxygen-containing gases, for about 5 to 30 minutes at a temperature in the range between about 80° to 150° C. and a pressure in the range between about 0.3013 to 3.1013 MPa, thereby producing a substantially cobalt-free organic hydroformylation reaction product and a water soluble cobaltous salt aqueous product, and separating said substantially cobalt-free crude product from said water soluble cobaltous salt aqueous product.

17. The method according to claim 16 wherein said water present in an amount between about 5 to 50 wt. %, based upon the feed rate of said crude product, and said organic acid is present in an amount between about 0.1 to 5 wt. %, based upon the feed rate of said crude product.

18. The method according to claim 16 wherein said demetalling step takes place within a trayed column or pipe-reactor.

19. A method for producing higher aldehydes and higher alcohols which comprises:

hydroformylating an olefinic feedstock with synthesis gas in the presence of a cobalt-containing catalyst to form a crude product containing higher aldehyde, higher alcohol, secondary products and dissolved cobalt catalysts;

removing said cobalt catalysts from said crude product by the following steps: (a) contacting said crude product with an organic acid and water, in the absence of any oxygen-containing gases, thereby producing a substantially cobalt-free organic hydroformylation reaction product and a water soluble cobaltous salt aqueous product; (b) separating said substantially cobalt-free crude product from said water soluble cobaltous salt aqueous product; (c) diverting said substantially cobalt-free organic hydroformylation reaction product for further downstream treatment such as distillation or hydrogenation; (d) concentrating the water soluble cobaltous salt aqueous product thereby producing a concentrated aqueous solution of cobaltous salt and a substantially cobalt-free water containing said organic acid, whereby said concentrated aqueous solution of cobaltous salt is separated from said substantially cobalt-free water containing said organic acid; (e) recycling said substantially cobalt-free water containing said organic acid to step (a); (f) contacting said concentrated aqueous solution of cobaltous salt with an alcohol stream and synthesis gas, and passing this mixture to a preformer reactor where said concentrated aqueous solution of cobaltous salt is converted to a cobalt carbonyl; (g) contacting said cobalt carbonyl with a stream of stripping gas to entrain volatile cobalt compounds in said stripping gas and to generate as bottoms alcohol products and dissolved cobaltous salts; whereby said entrained volatile cobalt compounds are taken out overhead and the alcohol products and dissolved cobaltous salts are taken out as bottoms; (h) separating said alcohol products produced in step (g) from said dissolved cobaltous salt; (i) recycling said alcohol from step (h) to step (f); (j) recycling said dissolved cobaltous salt from step (h) to step (a); and (k) contacting said volatile cobalt compounds from step (g) with said olefinic feedstock; whereby said volatile cobalt compounds are absorbed into said olefinic feedstock; and recycling said contacted liquid olefinic feedstock from step (k) to said hydroformylation step.

20. A method for producing higher aldehydes and higher alcohols which comprises:

hydroformylating an olefinic feedstock with synthesis gas in the presence of a cobalt-containing catalyst to form a crude product containing higher aldehyde, higher alcohol, secondary products and dissolved cobalt catalysts;

removing said cobalt catalysts from said crude product by the following steps: (a) contacting said crude product with water and an organic acid; (b) contacting the product of step (a) with a stream of stripping gas to entrain volatile cobalt compounds in said stripping gas; whereby said entrained volatile cobalt compounds are taken out overhead, and organic hydroformylation reaction products containing water soluble cobaltous salts and water soluble cobalt carbonyls dissolved therein are taken out as bottoms; (c) separating said water soluble cobaltous salts and water soluble cobalt carbonyl of step (b) from said organic hydroformylation reaction product; (d) diverting said organic hydroformylation reaction product of step (c) for further downstream treatment such as distillation or hydrogenation; (e) contacting said water soluble cobaltous salts and water soluble cobalt carbonyl of step (c) with a stream of organic acid, water and at least a portion of said organic hydroformylation reaction product, in the absence of any oxygen-containing gases, thereby converting said water soluble cobalt carbonyl to a cobaltous salt and forming a water soluble cobaltous salt aqueous product; (f) concentrating the water soluble cobaltous salt aqueous product from step (e) thereby producing a concentrated aqueous solution of cobaltous salt and a substantially cobalt-free water containing said organic acid, whereby said concentrated aqueous solution of cobaltous salt is separated from said substantially cobalt-free water containing said organic acid; (g) recycling said substantially cobalt-free water containing said organic acid to step (b); (h) contacting said concentrated aqueous solution of cobaltous salt with an alcohol stream, an oxonation product and/or a hydrogenation product and synthesis gas, and passing this mixture to a preformer reactor where said concentrated aqueous solution of cobaltous salt is converted to a cobalt carbonyl; (i) recycling the cobalt carbonyl produced in step (h) to step (a); and (j) contacting said volatile cobalt compounds from step (b) with said olefinic feedstock, whereby said volatile cobalt compounds are absorbed into said olefinic feedstock; and recycling said contacted liquid olefinic feedstock from step (j) to said hydroformylation step.

21. The method according to claim 20 wherein step (e) also produces a substantially cobalt-free hydroformylation product which is recycled to step (b).

* * * * *